United States Statutory Invention Registration [19]

[11] Reg. Number: H350

Adolph et al. [43] Published: Oct. 6, 1987

[54] ENERGETIC POLYNITRO FORMAL PLASTICIZERS

[75] Inventors: Horst D. Adolph, Silver Spring; Kyung E. Kim, Potomac, both of Md.

[73] Assignee: The United States of America as represented by the Secretary of the Navy, Washington, D.C.

[21] Appl. No.: 43,268

[22] Filed: Apr. 27, 1987

[51] Int. Cl.[4] ..... C06B 25/00; C07C 79/343; C07B 43/303

[52] U.S. Cl. ..... 149/88; 568/590; 568/944

*Primary Examiner*—John F. Terapane
*Assistant Examiner*—J. E. Thomas
*Attorney, Agent, or Firm*—K. E. Walden; Roger D. Johnson

[57] ABSTRACT

An energetic plasticizer which is a mixture of bis(2,2,2-trinitroethyl)formal, bis(2,2-dinitropropyl)formal, and a new compound 2,2-dinitropropyl 2,2,2-trinitroethyl formal.

4 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ENERGETIC POLYNITRO FORMAL PLASTICIZERS

BACKGROUND OF THE INVENTION

This invention relates to organic formals and more particularly to polynitro organic formals.

Plasticizers which are commonly used in gun propellants and other energetic compositions are nitroglycerin (NG), butanetriol trinitrate (BTTN), metriol trinitrate (METN), diethylene glycol dinitrate (DEGN), and bis(2,2-dinitropropyl)formal/acetal (BDNPF/A). Disadvantages which these materials exhibit are low thermal stability due to the presence of secondary hydroxy groups (NG, BTTN), low energy (BDNPF/A, METN, DEGN), and high vapor pressure (DEGN, NG).

SUMMARY OF THE INVENTION

Accordingly, an object of this invention is to provide a new energetic plasticizer.

Another object of this invention is to provide an improved energetic plasticizer having a low vapor pressure.

A further object of this invention is to provide an improved plasticizer having a low melting point.

Yet another object of this invention is to provide an improved plasticizer which has good thermal stability.

These and other objects of this invention are accomplished by providing energetic plasticizers which are binary and ternary mixtures of bis(2,2-dinitropropyl)formal (BDNPF), bis(2,2,2-trinitroethyl)formal (TEFO), and 2,2-dinitropropyl 2,2,2-trinitroethyl formal (TNEPF).

DETAILED DESCRIPTION OF THE PREFERRED EMBODIMENT

This invention provides binary and ternary mixtures of bis(2,2-dinitropropyl)formal (BDNPF), bis(2,2,2-trinitroethyl)formal (TEFO), and a new compound 2,2-dinitropropyl 2,2,2-trinitroethyl formal (TNEPF) which are plasticizers for energetic explosive and propellant compositions. These mixtures are particularly suitable for plasticizing polymers such as cellulose acetate butyrate (CAB), nitrocellulose (NC), polyethylene glycol (PEG), and polycaprolactone (PCP). The plasticized polymers are usually prepared from a solution of the plasticizer mixture and polymer in a common volatile solvent, such as ethyl acetate, by removal of the solvent.

The composition of the plasticizer mixture can vary substantially and is selected according to energy content and melting point desired for a specific use. For instance, the lowest melting mixture in the TNEPF-/TEFO/BDNPF system was found to be a 30/70 mol percent mixture of TEFO/BDNPF which melts at approximately 19° C. This mixture is a plasticizer for applications where a low melting point is desired and energy content does not need to be maximized. It is prepared by mixing the appropriate amounts (3:7 molar ratio or 1:1.95 weight ratio) of TEFO and BDNPF which are known compounds.

A more energetic plasticizer mixture which has an acceptable melting point for gun propellant applications is composed of TNEPF and an approximately 1:1 (molar ratio) mixture of TEFO/BDNPF. Such mixtures were found to melt at 28°±1° C. when the TNEPF:TEFO:BDNPF molar ratios are from about 0.6:1:1 to 7 about 2.5:1:1. One such mixture having a molar ratio of about 2:1:1 is prepared by reacting a 1:1 mixture of dinitropropanol and trinitroethanol with 0.5 equivalents of formaldehyde dissolved in strong sulfuric acid as illustrated in the following equation and described in the example.

$$CH_3C(NO_2)_2CH_2OH + C(NO_2)_3CH_2OH + CH_2O \xrightarrow{80\%\ H_2SO_4} CH_3C(NO_2)_2CH_2OCH_2OCH_2C(NO_2)_3 + CH_3C(NO_2)_2CH_2OCH_2OCH_2C(NO_2)_2CH_3 + C(NO_2)_3CH_2OCH_2OCH_2C(NO_2)_3$$

TNEPF BDNPF TEFO

The TNEPF:TEFO:BDNPF molar ratio may be lowered from the 2.0:1:1 molar-ratio produced in the example down to the preferred lower limit 0.6:1:1 or lower by adding a 1:1 molar ratio TEFO/BDNPF mixture. The TNEPF:TEFO:BDNPF molar ratio may be raised from 2.0:1:1 to the preferred upper limit 2.5:1:1 or higher by adding TNEPF to the mixture.

Pure 2,2-dinitropropyl 2,2,2-trinitoethyl formal (TNEPF) can be isolated from the TNPF:TEFO:BDNPF 2:1:1 molar ratio mixture produced in the process of the example by preparative liquid chromatography.

The composition of the various plasticizer mixtures described here can be estimated from the $^1H$ NMR spectra obtained under high resolution conditions which permits separate integration of several formal and dinitropropyl methylene peaks.

TNEPF is a new composition of matter. It has a melting point of 40°–42° C. It is useful to depress the melting point of TEFO/BDNPF mixtures while maintaining a relatively high energy level. For example, a 1:1 molar mixture of TEFO and BDNPF melts at 31° C. Addition of TNEPF to a molar ratio from 0.6:1:1 to 15 2.5:1:1 lowers the melting point to 28°±1° C. and decreases the rate of crystallization while keeping the energy level constant. The general advantages of the binary and ternary mixtures of TNEPF, TEFO and BDNPF are very low volatility and good thermal stability (better than NG, BTTN) coupled with a relatively high energy content (higher than BDNPF/A, DEGDN, TMETN) and acceptable melting points. Due to the low vapor pressure, the handling and toxicity characteristics of the new plasticizers are also desirable. Thus, the overall properties of the binary and ternary plasticizer mixtures described here make them very desirable plasticizer mixtures which can be advantageously used in place of BDNPF/A, TMETN, or BTTN in many applications.

To more clearly illustrate this invention, the following example is presented. It should be understood, however, that this example is presented merely as a means of illustration and is not intended to limit the scope of the invention in any way.

EXAMPLE

Preparation of a 2:1:1 molar mixture of TNEPF, TEFO, and BDNPF

To a mixture of 120 g (0.663 mol) of 2,2,2-trinitroethanol, 118.8 g (0.792 mol) of 2,2-dinitropropanol, and about 20 mL of dichloromethane was added, with stirring and ice-cooling, a solution of 20 g of paraformaldehyde (i.e., 0.667 mol of formaldehyde) in 375 mL of 82 percent sulfuric acid. The mixture was stirred at room temperature overnight, and then poured over crushed ice. The product was extracted with dichloromethane, and the extracts were washed with 5 percent aqueous $NaHCO_3$ until the $NaHCO_3$ solution remained essentially colorless. The organic phase was then dried ($MgSO_4$) and freed from solvent in vacuo. Obtained was 161.4 g of the 2:1:1 formal mixture (65.2 percent yield).

Obviously numerous modifications and variations of the present invention are possible in light of the above teachings. It is therefore to be understood that within the scope of the appended claims the invention may be practiced otherwise than as specifically described herein.

What is claimed is:

1. 2,2-dinitropropyl 2,2,2-trinitroethyl formal, $CH_3C(NO_2)_2CH_2OCH_2OCH_2C(NO_2)_3$.

2. An energetic plasticizer comprising a mixture of 2,2-dinitropropyl 2,2,2-trinitroethyl formal, bis(2,2,2-trinitroethyl)formal, and bis(2,2-dinitropropyl)formal.

3. The energetic plasticizer of claim 2 wherein the molar ratio of 2,2-dinitropropyl 2,2,2-trinitroethyl formal to bis(2,2,2-trinitroethyl)formal to bis(2,2-dinitropropyl)formal is from 0.6:1:1 to 2.5:1:1.

4. The energetic plasticizer of claim 3 wherein the molar ratio of 2,2-dinitropropyl 2,2,2-trinitroethyl formal to bis(2,2,2-trinitroethyl)formal to bis(2,2-dinitropropyl)formal is about 2:1:1.

* * * * *